(12) United States Patent
Takagaki et al.

(10) Patent No.: US 8,980,914 B2
(45) Date of Patent: Mar. 17, 2015

(54) THERAPEUTIC AGENT FOR CHRONIC OBSTRUCTIVE PULMONARY DISEASE AND METHOD FOR TREATMENT FOR CHRONIC OBSTRUCTIVE PULMONARY DISEASE WITH THE SAME

(75) Inventors: Hidetsugu Takagaki, Sakura (JP); Yasuo Aoki, Yotsukaido (JP); Mitsuteru Ishiwara, Sakura (JP); Nobuaki Mizutani, Sakura (JP)

(73) Assignee: Mariposa Health Limited, Bilgola Plateau NSW (AU)

( * ) Notice: Subject to any disclaimer, the term of this patent is extended or adjusted under 35 U.S.C. 154(b) by 498 days.

(21) Appl. No.: 10/565,828

(22) PCT Filed: Jul. 27, 2004

(86) PCT No.: PCT/JP2004/011013
§ 371 (c)(1),
(2), (4) Date: Jan. 25, 2006

(87) PCT Pub. No.: WO2005/012251
PCT Pub. Date: Feb. 10, 2005

(65) Prior Publication Data
US 2006/0235045 A1    Oct. 19, 2006

(30) Foreign Application Priority Data

Jul. 30, 2003 (JP) ................. 2003-203699

(51) Int. Cl.
*A61K 31/00* (2006.01)
*A61K 31/4704* (2006.01)
*C07D 215/38* (2006.01)

(52) U.S. Cl.
CPC ................... *C07D 215/38* (2013.01)
USPC ....................................... 514/310

(58) Field of Classification Search
CPC ... A61K 31/00; A61K 31/4704; C07D 215/38
USPC ....................................... 514/310
See application file for complete search history.

(56) References Cited

U.S. PATENT DOCUMENTS

| 5,942,521 A | 8/1999 | Takagaki et al. |
| 6,114,352 A * | 9/2000 | Takagaki et al. ............... 514/312 |
| 6,136,822 A | 10/2000 | Takagaki et al. |
| 6,624,181 B1 * | 9/2003 | Kilian et al. .................. 514/352 |

FOREIGN PATENT DOCUMENTS

| EP | 0785190 A2 | 7/1997 |
| EP | 1270006 A2 | 1/2003 |
| JP | 09-255659 | 9/1997 |

OTHER PUBLICATIONS

Kimura et al. (Chem. Pharm. Bull. (2001); 49(10):1321-1325).*
Postma et al. (Am J Respir Crit Care Med. (1998); 158(5 Pt 3):S187-92).*
Aoki Y., Ishihara M., Koda A., Takagaki H., Eur. J. Pharmacol. (2000); 409:325-330.*
Zhou et al. (Zhonghua Jie He He Hu Xi Za Zhi. Sep. 2006;29(9):577-82).*
Mizutani et al. (Biol. Pharm. Bull.: Regular Article: Pharmacology; "Pulmonary emphysema induced by cigarette smoke solution and lipopolysaccharide in guinea pigs").*
Mizutani et al. ("Pulmonary emphysema induced by cigarette smoke solution and lipopolysaccharide in guinea pigs". Biol. Pharm. Bull. Sep. 2009;32(9):1559-64.*
Y. Aoki; "Inhibitory effect of a novel quinolinone derivative, TA-270, on asthmatic inflammatory responses in sensitized guinea pigs;" *European Journal of Pharmacology*; vol. 409; No. 3; 2000; pp. 325-330.
J.E. Repine, et al.; "Oxidative Stress in Chronic Obstructive Pulmonary Disease;" *American Journal of Respiratory and Critical Care Medicine*; vol. 156; 1997; pp. 341-357.
Yasuo Aoki et al., "Inhibitory effect of a novel quinolinone derivative, TA-270, on asthmatic inflammatory responses in sensitized guinea pigs," European Journal of Pharmacology 409(2000) pp. 325-330.
Masakazu Ichinose et al., "Increase in Reactive Nitrogen Species Production in Chronic Obstructive Pulmonary Disease Airways," Am J Respir Crit Care Med, vol. 162, pp. 701-706, 2000.
Brain J. Dykstra et al., "Lung Volumes in 4,774 Patients with Obstructive Lung Disease," Chest 1999, 115, pp. 68-74.
Peter Thomas et al., "Theophylline and Salbutamol Improve Pulmonary Function in Patients with Irreversible Chronic Obstructive Pulmonary Disease," Chest 1999, 115, pp. 160-165.

(Continued)

*Primary Examiner* — Jeffrey S. Lundgren
*Assistant Examiner* — Chris Simmons
(74) *Attorney, Agent, or Firm* — Locke Lord LLP

(57) ABSTRACT

This therapeutic agent for chronic obstructive pulmonary disease comprises, an active ingredient, at least one of a 7-aminoquinolinone derivative represented by the general formula (I):

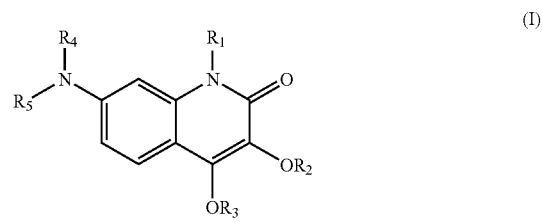

wherein $R_1$ represents a hydrogen atom or an alkyl group; $R_2$ and $R_3$ each represents a group selected from a hydrogen atom, an acyl group, an alkyl group and an alkenyl group; and $R_4$ and $R_5$ each represents a group selected from a hydrogen atom, an acyl group, an alkyl group, an alkenyl group and an aralkyl group, and its physiologically acceptable salt.

14 Claims, No Drawings

(56) References Cited

OTHER PUBLICATIONS

"Global Initiative for Chronic Obstructive Lung Disease," Global Strategy for the Diagnosis, Management, and Prevention of Chronic Obstructive Pulmonary Disease, Updated 2005 (55 sheets).

"The Merk Manual of diagnosis and therapy" 1999, Gary Zelko, USA, XP002485275—p. 568-p. 569.

G. M. Coppola, "The Chemistry of 2*H*-3, 1-Benzoxazine-2,4(1*H*)-dione (Isatoic Anhydride). 18[1]. A Short Synthesis of Swietenidin A," Journal of Heterocyclic Chemistry 22, 1985, pp. 1087-1088.

"NAEPP Expert Panel Report, Guideline for the Diagnosis and Management of Asthma—Update of Selected Topics 2002," NHLBI, 2002, 6 sheets.

R. A. Pauwels et al., "Global Strategy for the Diagnosis, Managements, and Prevention of Chronic Obstructive Pulmonary Disease," NHLBI/WHO Workshop Summary, 2001, pp. 1256-1277.

R. E. Giles et al. "Use of an Analog On-Line Computer for the Evaluation of Pulmonary Resistance and Dynamic Compliance in the Anesthetized Dog," Arch. Int. Pharmacodyn. 194, 1971, pp. 213-222.

J.P. Crow, "Dichlorodihydrofluorescein and Dihydrorhodamine 123 Are Sensitive Indicators of Peroxynitrite in Vitro: Implications for Intracellular Measurement of Reactive Nitrogen and Oxygen Species," Nitric Oxide: Biology and Chemistry vol. 1, 1997, pp. 145-157.

The English translation for Y. Yoshiwasa et al., "How to Use Steroid Drugs" ("Steroid-yaku no Tsukaikata,") Mdicina, vol. 30, No. 12, 1993, pp. 2148-2149.

Michiyoshi Harasawa Editorial supervisor, Satoshi Kitamura Compiler, Additional Volume of Journal of Clinical and Experimental Medicine, Respiratory Disease (Ver. 3), Ishiyaku Publishers, Inc., 1999, pp. 210 to 213, pp. 345 to 347, with partial English translation thereof.

Office Action mailed Jul. 20, 2010, issued on Japanese Patent Application No. 2004-072488 with English translation thereof.

\* cited by examiner

THERAPEUTIC AGENT FOR CHRONIC OBSTRUCTIVE PULMONARY DISEASE AND METHOD FOR TREATMENT FOR CHRONIC OBSTRUCTIVE PULMONARY DISEASE WITH THE SAME

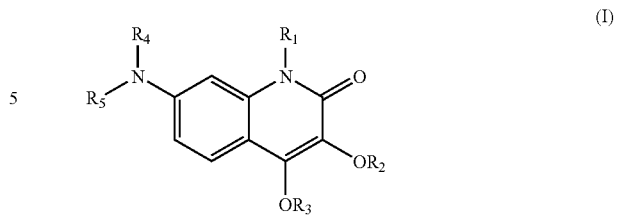

TECHNICAL FIELD

The present invention relates to a therapeutic agent for chronic obstructive pulmonary disease comprising, as an active ingredient, a 7-aminoquinolinone derivative and its physiologically acceptable salt, which is useful for treating chronic obstructive pulmonary disease, and a method for treating chronic obstructive pulmonary disease using the same.

BACKGROUND ART

With respect to a quinolinone derivative, general quinolinone derivatives such as 3-methoxy-4-hydroxy-1-methyl-2(1H)-quinolinone and 8-methoxy-3-methoxy-4-hydroxy-1-methyl-2(1H)-quinolinone have hitherto been known (see, for example, Non-Patent Document 1: "Journal of Heterocyclic Chemistry 22, pages 1087-1088, 1985 (J. Heterocyclic Chem., 22, 1985)"). However, such a document does not describe that these compounds are useful as a specific therapeutic agent.

Also there have been known quinolinone derivatives which have oxygens directly bonded to carbons at the 3- and 4-positions and also have an amino group at the 7-position (see, for example, Patent Document 1: specification of U.S. Pat. No. 5,942,521 and Patent Document 2: specification of U.S. Pat. No. 6,136,822). In these documents, although an antiallergic action and an asthma treating action of a quinolinone derivative having an amino group have been studied, a therapeutic action against specific symptoms of chronic obstructive pulmonary disease through no antigen-antibody reaction has never been studied and also it has never been known that such a quinolinone derivative is effective as a therapeutic agent for chronic obstructive pulmonary disease.

An object to be achieved by the present invention is to provide a therapeutic agent for chronic obstructive pulmonary disease, which has high safety and is effective on chronic obstructive pulmonary disease and also exhibits extremely excellent drug potency, and a method for treating chronic obstructive pulmonary disease using the same.

DISCLOSURE OF THE INVENTION

To achieve the above object, the present inventors have synthesized various compounds and evaluated drug potency and safety thereof. As a result, they have found that a specific aminoquinolinone derivative is extremely excellent as a therapeutic agent for chronic obstructive pulmonary disease, and thus the present invention has been completed.

That is, the present invention is directed to a therapeutic agent for chronic obstructive pulmonary disease comprising, as an active ingredient, at least one of a 7-aminoquinolinone derivative represented by the general formula (I):

wherein $R_1$ represents a hydrogen atom or an alkyl group; $R_2$ and $R_3$ each represents a group selected from a hydrogen atom, an acyl group, an alkyl group and an alkenyl group; and $R_4$ and $R_5$ each represents a group selected from a hydrogen atom, an acyl group, an alkyl group, an alkenyl group and an aralkyl group, and its physiologically acceptable salt.

That is, the present invention is directed to use of at least one of the 7-aminoquinolinone derivative and its physiologically acceptable salt for treating chronic obstructive pulmonary disease.

Also, the present invention is directed to a therapeutic agent for chronic obstructive pulmonary disease comprising, as an active ingredient, the 7-aminoquinolinone derivative of the above general formula (1) and its physiologically acceptable salt, wherein the chronic obstructive pulmonary disease is chronic bronchitis or pulmonary emphysema. That is, the present invention is directed to use of at least one of the 7-aminoquinolinone derivative and its physiologically acceptable salt for treating chronic bronchitis and pulmonary emphysema.

Furthermore, the present invention is directed to a method for treating chronic obstructive pulmonary disease, which comprises using the 7-aminoquinolinone derivative and its physiologically acceptable salt.

The present invention can provide a therapeutic agent for chronic obstructive pulmonary disease, which has high safety and also exhibits extremely excellent drug potency to chronic obstructive pulmonary disease, by using at least one of a specific 7-aminoquinolinone derivative and its physiologically acceptable salt as an active ingredient. That is, in the present invention, at least one of the 7-aminoquinolinone derivative and its physiologically acceptable salt is effective for treating chronic obstructive pulmonary disease.

BEST MODE FOR CARRYING OUT THE INVENTION $R_1$ in the 7-aminoquinolinone derivative represented by the general formula (I):

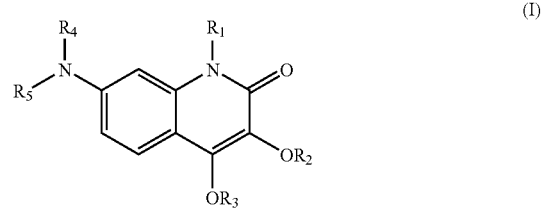

of the present invention is a hydrogen atom or an alkyl group. The alkyl group in $R_1$ may be a linear or branched alkyl group.

Specific examples of the alkyl group include methyl group, ethyl group, propyl group, isopropyl group, n-butyl group, s-butyl group, n-pentyl group, hexyl group, octyl group and decyl group, and the alkyl group is preferably an alkyl group having 1 to 10 carbon atoms, and more preferably 1 to 8 carbon atoms.

$R_2$ and $R_3$ of the general formula (I) are a hydrogen atom, an acyl group, an alkyl group or an alkenyl group. Examples of the acyl group include alkanoyl group such as formyl group, acetyl group, propionyl group or butyryl group, and benzoyl group. The benzoyl group may have a substituent and examples thereof include p-hydroxybenzoyl group, p-methoxybenzoyl group, 2,4-dihydroxybenzoyl group and 2,4-dimethoxybenzoyl group. An alkanoyl group is preferable and an acetyl group is particularly preferable.

The alkyl group as for $R_2$ and $R_3$ may be a linear or branched alkyl group, and examples thereof include methyl group, ethyl group, propyl group, isopropyl group, n-butyl group, s-butyl group, n-pentyl group, hexyl group, octyl group and decyl group, and the alkyl group is preferably an alkyl group having 1 to 10 carbon atoms, and more preferably an alkyl group having 1 to 8 carbon atoms.

The alkenyl group as for $R_2$ and $R_3$ may be a linear or branched alkenyl group, and examples thereof include vinyl group, propenyl group, hexenyl group, octenyl group, prenyl group and geranyl group, and the alkenyl group is preferably an alkenyl group having 2 to 10 carbon atoms.

In the general formula (I), $R_4$ and $R_5$ may be the same or different and represent a hydrogen atom, an acyl group, an alkyl group, an alkenyl group or an aralkyl group. Examples of the acyl group include alkanoyl group such as formyl group, acetyl group, propionyl group or butyryl group, benzoyl group, substituted benzoyl group, or cynnamoyl group which may be substituted.

Examples of the substituted benzoyl group include p-hydroxybenzoyl group, p-methoxybenzoyl group, 2,4-dihydroxybenzoyl group and 2,4-dimethoxybenzoyl group. Examples of the cinnamoyl group which may be substituted include cinnamoyl group, 2-hydroxycinnamoyl group, 3-hydroxycinnamoyl group, 4-hydroxycinnamoyl group, 3,4-dihydroxycinnamoyl group, 4-hydroxy-3-methoxycinnamoyl group, 3-hydroxy-4-methoxycinnamoyl group and 3,5-dimethoxy-4-hydroxycinnamoyl group. The cinnamoyl group is preferably cinnamoyl group which may be substituted.

The alkyl group as for $R_4$ and $R_5$ of the general formula (I) may be a linear or branched alkyl group, and examples thereof include methyl group, ethyl group, propyl group, isopropyl group, n-butyl group, s-butyl group, n-pentyl group, hexyl group, octyl group and decyl group. The alkyl group is preferably an alkyl group having 1 to 10 carbon atoms, and more preferably 1 to 8 carbon atoms.

The alkenyl group as for $R_4$ and $R_5$ may be a linear or branched alkenyl group, and examples thereof include vinyl group, propenyl group, hexenyl group, octenyl group, prenyl group and geranyl group. The alkenyl group is preferably an alkenyl group having 2 to 10 carbon atoms.

Examples of the aralkyl group as for $R_4$ and $R_5$ include aralkyl groups such as benzyl group and substituted benzyl group (for example, p-methoxybenzyl group or p-hydroxybenzyl group). The present invention also includes a 7-aminoquinolinone derivative in which substituents as for $R_4$ and $R_5$ of the 7-aminoquinolinone derivative represented by the general formula (I) are the same substituents, and a 7-aminoquinolinone derivative in which different substituents selected from the above group are combined.

The 7-aminoquinolinone derivative as the active ingredient of the therapeutic agent for chronic obstructive pulmonary disease of the present invention can be prepared by appropriately selecting a preferable method according to the objective 7-aminoquinolinone derivative. For example, it can be prepared by the method described in Japanese Patent No. 2,943,725 or U.S. Pat. No. 6,136,822.

As an example, the method described in U.S. Pat. No. 6,136,822 will now be described.

By reacting an amide derivative represented by the general formula (II):

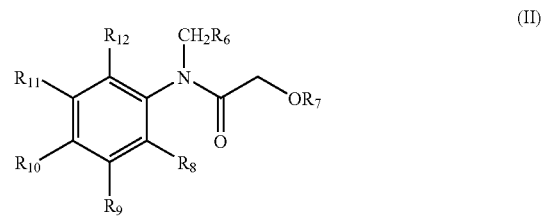

with a basic substance, an intramolecular cyclization reaction is carried out as shown in the following scheme:

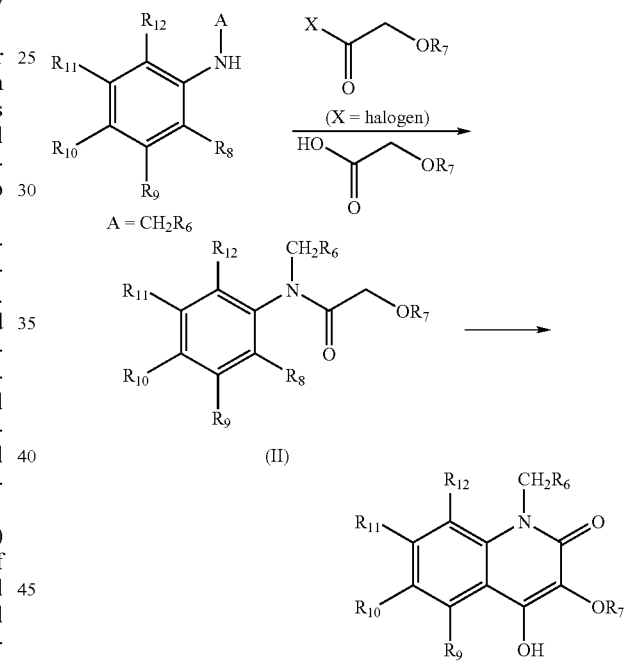

wherein $R_6$ represents a hydrogen atom, an alkyl group, an alkyl group having a hydroxyl group, an alkenyl group or an aryl group; $R_7$ represents an alkyl group, an alkenyl group, an aryl group or an aralkyl group; $R_8$ represents a reactive carboxyl group; $R_9$, $R_{10}$ and $R_{12}$ represent a hydrogen atom; and $R_{11}$ represents $R_{13}R_{14}N-$ (wherein $R_{13}$ and $R_{14}$ each independently represents a hydrogen atom, an alkyl group, an alkenyl group, an aralkyl group or an acyl group).

Examples of the basic substance include various compounds such as alkali metal, alkali metal alkoxide, alkali earth metal alkoxide, alkali metal hydride, alkali earth metal hydride and alkali metal amide.

Examples of the alkali metal include alkali metals such as sodium and potassium, examples of the alkali metal alkoxide include basic substances such as sodium methoxide, sodium ethoxide, sodium t-butoxide and potassium t-butoxide, and examples of the alkali earth metal alkoxide include magnesium methoxide, magnesium ethoxide, magnesium t-butoxide, calcium methoxide, calcium ethoxide, calcium t-butoxide, barium methoxide, barium ethoxide and barium t-butoxide.

Examples of the alkali metal hydride include alkali metal hydrides such as lithium hydride, sodium hydride and potassium hydride, and examples of the alkali earth metal hydride include alkali earth metal hydrides such as calcium hydride. Examples of the alkali metal amide include lithium amide, sodium amide, potassium amide, lithium diisopropylamide, lithium bis(trimethylsilyl)amide and sodium bis(trimethylsilyl)amide and potassium bis(trimethylsilyl)amide.

The amount of the basic substance required for the cyclization reaction is usually from 1 to 5 mols, and preferably from 2 to 3 mols, per mol of the amide derivative to be reacted. When sodium hydride, potassium t-butoxide or lithium diisopropylamide is used as the basic substance, enough amount is usually 2 mols per mol of the amide derivative.

The reaction in the method for preparing the 7-aminoquinolinone derivative is carried out in an organic solvent which does not inhibit the reaction. Examples of the organic solvent include hydrocarbon-based solvents such as benzene and toluene; alcohol-based solvents such as methanol, ethanol, propanol, isopropanol and t-butanol; ether-based solvents such as diethyl ether, tetrahydrofuran and 1,2-dimethoxyethane; and amide-based solvents such as N,N-dimethylformamide and 1-methyl-2-pyrolidinone.

Preferable organic solvent varies according to the kind of the basic substance to be used. For example, in case of the alkali metal alkoxide, an alcohol-based solvent is preferable. When the alkali metal amide such as lithium amide, sodium amide or potassium amide is used, ammonia can be used as the solvent.

The reaction temperature varies according to the kind of the basic substance and reaction solvent to be used, but is usually from −80° C. to 100° C., and preferably from −50° C. to 50° C., and the reaction time is usually from 1 to 5 hours.

Specific examples of the thus obtained 7-aminoquinolinone derivative represented by the general formula (I) of the present invention include compounds represented by the following Tables 1 to 17.

TABLE 1

| Compound No. | $R_1$ | $R_2$ | $R_3$ | $R_4$ | $R_5$ |
|---|---|---|---|---|---|
| 1 | H | Acetyl | Methyl | H | H |
| 2 | H | Acetyl | Butyl | H | H |
| 3 | H | Acetyl | Hexyl | H | H |
| 4 | H | Acetyl | 3-Methyl-2-butenyl | H | H |
| 5 | H | Acetyl | Geranyl | H | H |
| 6 | H | Acetyl | H | H | H |
| 7 | H | Formyl | Methyl | H | H |
| 8 | H | Formyl | Butyl | H | H |
| 9 | H | Formyl | Hexyl | H | H |
| 10 | H | Formyl | 3-Methyl-2-butenyl | H | H |
| 11 | H | Formyl | Geranyl | H | H |
| 12 | H | Formyl | H | H | H |
| 13 | H | Methyl | Methyl | H | H |
| 14 | H | Methyl | Butyl | H | H |
| 15 | H | Methyl | Hexyl | H | H |
| 16 | H | Methyl | 3-Methyl-2-butenyl | H | H |
| 17 | H | Methyl | Geranyl | H | H |
| 18 | H | Methyl | H | H | H |
| 19 | H | Isopropyl | H | H | H |
| 20 | H | Butyl | H | H | H |
| 21 | H | Hexyl | H | H | H |
| 22 | H | 2-Methyl-pentyl | H | H | H |
| 23 | H | Octyl | H | H | H |
| 24 | H | 2-Propenyl | H | H | H |
| 25 | H | Geranyl | H | H | H |
| 26 | H | H | H | H | H |
| 27 | H | H | Methyl | H | H |
| 28 | H | H | Butyl | H | H |
| 29 | H | H | Hexyl | H | H |
| 30 | H | H | 3-Methyl-2-butenyl | H | H |
| 31 | H | H | Geranyl | H | H |
| 32 | Methyl | Acetyl | Methyl | H | H |
| 33 | Methyl | Acetyl | Ethyl | H | H |
| 34 | Methyl | Acetyl | Butyl | H | H |
| 35 | Methyl | Acetyl | Hexyl | H | H |
| 36 | Methyl | Acetyl | 3-Methyl-2-butenyl | H | H |
| 37 | Methyl | Acetyl | Geranyl | H | H |
| 38 | Methyl | Acetyl | H | H | H |
| 39 | Methyl | Formyl | Methyl | H | H |
| 40 | Methyl | Formyl | Butyl | H | H |

TABLE 2

| Compound No. | $R_1$ | $R_2$ | $R_3$ | $R_4$ | $R_5$ |
|---|---|---|---|---|---|
| 41 | Methyl | Formyl | Hexyl | H | H |
| 42 | Methyl | Formyl | 3-Methyl-2-butenyl | H | H |
| 43 | Methyl | Formyl | Geranyl | H | H |
| 44 | Methyl | Formyl | H | H | H |
| 45 | Methyl | Methyl | Methyl | H | H |
| 46 | Methyl | Methyl | Butyl | H | H |
| 47 | Methyl | Methyl | Hexyl | H | H |
| 48 | Methyl | Methyl | 3-Methyl-2-butenyl | H | H |
| 49 | Methyl | Methyl | Geranyl | H | H |
| 50 | Methyl | Methyl | H | H | H |
| 51 | Methyl | Isopropyl | H | H | H |
| 52 | Methyl | Butyl | H | H | H |
| 53 | Methyl | Hexyl | H | H | H |
| 54 | Methyl | 2-Methyl-pentyl | H | H | H |
| 55 | Methyl | Octyl | H | H | H |
| 56 | Methyl | 2-Propenyl | H | H | H |
| 57 | Methyl | Geranyl | H | H | H |
| 58 | Methyl | H | Methyl | H | H |
| 59 | Methyl | H | Butyl | H | H |
| 60 | Methyl | H | Hexyl | H | H |
| 61 | Methyl | H | 3-Methyl-2-butenyl | H | H |
| 62 | Methyl | H | Geranyl | H | H |
| 63 | Methyl | H | H | H | H |
| 64 | Ethyl | Acetyl | Methyl | H | H |
| 65 | Ethyl | Acetyl | Ethyl | H | H |
| 66 | Ethyl | Acetyl | Butyl | H | H |
| 67 | Ethyl | Acetyl | Hexyl | H | H |
| 68 | Ethyl | Acetyl | 3-Methyl-2-butenyl | H | H |
| 69 | Ethyl | Acetyl | Geranyl | H | H |
| 70 | Ethyl | Acetyl | H | H | H |
| 71 | Ethyl | Formyl | Methyl | H | H |
| 72 | Ethyl | Formyl | Butyl | H | H |
| 73 | Ethyl | Formyl | Hexyl | H | H |
| 74 | Ethyl | Formyl | 3-Methyl-2-butenyl | H | H |
| 75 | Ethyl | Formyl | Geranyl | H | H |
| 76 | Ethyl | Formyl | H | H | H |
| 77 | Ethyl | Methyl | Methyl | H | H |
| 78 | Ethyl | Methyl | Butyl | H | H |
| 79 | Ethyl | Methyl | Hexyl | H | H |
| 80 | Ethyl | Methyl | 3-Methyl-2-butenyl | H | H |

TABLE 3

| Compound No. | $R_1$ | $R_2$ | $R_3$ | $R_4$ | $R_5$ |
|---|---|---|---|---|---|
| 81 | Ethyl | Methyl | Geranyl | H | H |
| 82 | Ethyl | Methyl | H | H | H |
| 83 | Ethyl | Isopropyl | H | H | H |
| 84 | Ethyl | Butyl | H | H | H |

TABLE 3-continued

| Compound No. | R$_1$ | R$_2$ | R$_3$ | R$_4$ | R$_5$ |
|---|---|---|---|---|---|
| 85 | Ethyl | Hexyl | H | H | H |
| 86 | Ethyl | 2-Methyl-pentyl | H | H | H |
| 87 | Ethyl | Octyl | H | H | H |
| 88 | Ethyl | 2-Propenyl | H | H | H |
| 89 | Ethyl | Geranyl | H | H | H |
| 90 | Ethyl | H | Methyl | H | H |
| 91 | Ethyl | H | Butyl | H | H |
| 92 | Ethyl | H | Hexyl | H | H |
| 93 | Ethyl | H | 3-Methyl-2-butenyl | H | H |
| 94 | Ethyl | H | Geranyl | H | H |
| 95 | Ethyl | H | H | H | H |
| 96 | Propyl | H | Methyl | H | H |
| 97 | Propyl | H | Propyl | H | H |
| 98 | Propyl | H | Butyl | H | H |
| 99 | Propyl | H | Decyl | H | H |
| 100 | Butyl | Acetyl | Methyl | H | H |
| 101 | Butyl | Acetyl | Ethyl | H | H |
| 102 | Butyl | Acetyl | Butyl | H | H |
| 103 | Butyl | Acetyl | Hexyl | H | H |
| 104 | Butyl | Acetyl | 3-Methyl-2-butenyl | H | H |
| 105 | Butyl | Acetyl | Geranyl | H | H |
| 106 | Butyl | Acetyl | H | H | H |
| 107 | Butyl | Formyl | Methyl | H | H |
| 108 | Butyl | Formyl | Butyl | H | H |
| 109 | Butyl | Formyl | Hexyl | H | H |
| 110 | Butyl | Formyl | 3-Methyl-2-butenyl | H | H |
| 111 | Butyl | Formyl | Geranyl | H | H |
| 112 | Butyl | Formyl | H | H | H |
| 113 | Butyl | Methyl | Methyl | H | H |
| 114 | Butyl | Methyl | Butyl | H | H |
| 115 | Butyl | Methyl | H | H | H |
| 116 | Butyl | Isopropyl | H | H | H |
| 117 | Butyl | Butyl | H | H | H |
| 118 | Butyl | Hexyl | H | H | H |
| 119 | Butyl | 2-Methyl-pentyl | H | H | H |
| 120 | Butyl | Octyl | H | H | H |

TABLE 4

| Compound No. | R$_1$ | R$_2$ | R$_3$ | R$_4$ | R$_5$ |
|---|---|---|---|---|---|
| 121 | Butyl | 2-Propenyl | H | H | H |
| 122 | Butyl | Geranyl | H | H | H |
| 123 | Butyl | H | Methyl | H | H |
| 124 | Butyl | H | Butyl | H | H |
| 125 | Butyl | H | Hexyl | H | H |
| 126 | Butyl | H | 3-Methyl-2-butenyl | H | H |
| 127 | Butyl | H | Geranyl | H | H |
| 128 | Butyl | H | H | H | H |
| 129 | Hexyl | Acetyl | Methyl | H | H |
| 130 | Hexyl | Acetyl | Ethyl | H | H |
| 131 | Hexyl | Acetyl | Butyl | H | H |
| 132 | Hexyl | Acetyl | Hexyl | H | H |
| 133 | Hexyl | Acetyl | 3-Methyl-2-butenyl | H | H |
| 134 | Hexyl | Acetyl | Geranyl | H | H |
| 135 | Hexyl | Acetyl | H | H | H |
| 136 | Hexyl | Formyl | Methyl | H | H |
| 137 | Hexyl | Formyl | Butyl | H | H |
| 138 | Hexyl | Formyl | Hexyl | H | H |
| 139 | Hexyl | Formyl | 3-Methyl-2-butenyl | H | H |
| 140 | Hexyl | Formyl | Geranyl | H | H |
| 141 | Hexyl | Formyl | H | H | H |
| 142 | Hexyl | Methyl | Methyl | H | H |
| 143 | Hexyl | Methyl | Butyl | H | H |
| 144 | Hexyl | Methyl | H | H | H |
| 145 | Hexyl | Isopropyl | H | H | H |
| 146 | Hexyl | Butyl | H | H | H |
| 147 | Hexyl | Hexyl | H | H | H |
| 148 | Hexyl | 2-Methyl-pentyl | H | H | H |
| 149 | Hexyl | Octyl | H | H | H |
| 150 | Hexyl | 2-Propenyl | H | H | H |
| 151 | Hexyl | Geranyl | H | H | H |
| 152 | Hexyl | H | Methyl | H | H |

TABLE 4-continued

| Compound No. | R$_1$ | R$_2$ | R$_3$ | R$_4$ | R$_5$ |
|---|---|---|---|---|---|
| 153 | Hexyl | H | Butyl | H | H |
| 154 | Hexyl | H | Hexyl | H | H |
| 155 | Hexyl | H | 3-Methyl-2-butenyl | H | H |
| 156 | Hexyl | H | Geranyl | H | H |
| 157 | Hexyl | H | H | H | H |
| 158 | Octyl | Acetyl | Methyl | H | H |
| 159 | Octyl | Acetyl | Ethyl | H | H |
| 160 | Octyl | Acetyl | Butyl | H | H |

TABLE 5

| Compound No. | R$_1$ | R$_2$ | R$_3$ | R$_4$ | R$_5$ |
|---|---|---|---|---|---|
| 161 | Octyl | Acetyl | Hexyl | H | H |
| 162 | Octyl | Acetyl | 3-Methyl-2-butenyl | H | H |
| 163 | Octyl | Acetyl | Geranyl | H | H |
| 164 | Octyl | Acetyl | H | H | H |
| 165 | Octyl | Formyl | Methyl | H | H |
| 166 | Octyl | Formyl | Butyl | H | H |
| 167 | Octyl | Formyl | Hexyl | H | H |
| 168 | Octyl | Formyl | 3-Methyl-2-butenyl | H | H |
| 169 | Octyl | Formyl | Geranyl | H | H |
| 170 | Octyl | Formyl | H | H | H |
| 171 | Octyl | Methyl | Methyl | H | H |
| 172 | Octyl | Methyl | Butyl | H | H |
| 173 | Octyl | Methyl | H | H | H |
| 174 | Octyl | Isopropyl | H | H | H |
| 175 | Octyl | Butyl | H | H | H |
| 176 | Octyl | Hexyl | H | H | H |
| 177 | Octyl | 2-Methyl-pentyl | H | H | H |
| 178 | Octyl | Octyl | H | H | H |
| 179 | Octyl | 2-Propenyl | H | H | H |
| 180 | Octyl | Geranyl | H | H | H |
| 181 | Octyl | H | Methyl | H | H |
| 182 | Octyl | H | Butyl | H | H |
| 183 | Octyl | H | Hexyl | H | H |
| 184 | Octyl | H | 3-Methyl-2-butenyl | H | H |
| 185 | Octyl | H | Geranyl | H | H |
| 186 | Octyl | H | H | H | H |
| 187 | H | Acetyl | Methyl | H | Hexyl |
| 188 | H | Acetyl | Butyl | H | Hexyl |
| 189 | H | Acetyl | Hexyl | H | Hexyl |
| 190 | H | Acetyl | 3-Methyl-2-butenyl | H | Hexyl |
| 191 | H | Acetyl | Geranyl | H | Hexyl |
| 192 | H | Acetyl | H | H | Hexyl |
| 193 | H | Formyl | Methyl | H | Hexyl |
| 194 | H | Formyl | Butyl | H | Hexyl |
| 195 | H | Formyl | Hexyl | H | Hexyl |
| 196 | H | Formyl | 3-Methyl-2-butenyl | H | Hexyl |
| 197 | H | Formyl | Geranyl | H | Hexyl |
| 198 | H | Formyl | H | H | Hexyl |
| 199 | H | Methyl | Methyl | H | Hexyl |
| 200 | H | Methyl | Butyl | H | Hexyl |

TABLE 6

| Compound No. | R$_1$ | R$_2$ | R$_3$ | R$_4$ | R$_5$ |
|---|---|---|---|---|---|
| 201 | H | Methyl | Hexyl | H | Hexyl |
| 202 | H | Methyl | 3-Methyl-2-butenyl | H | Hexyl |
| 203 | H | Methyl | Geranyl | H | Hexyl |
| 204 | H | Methyl | H | H | Hexyl |
| 205 | H | Isopropyl | H | H | Hexyl |
| 206 | H | Butyl | H | H | Hexyl |
| 207 | H | Hexyl | H | H | Hexyl |
| 208 | H | 2-Methyl-pentyl | H | H | Hexyl |
| 209 | H | Octyl | H | H | Hexyl |
| 210 | H | 2-Propenyl | H | H | Hexyl |
| 211 | H | Geranyloxy | H | H | Octyl |

TABLE 6-continued

| Compound No. | R₁ | R₂ | R₃ | R₄ | R₅ |
|---|---|---|---|---|---|
| 212 | H | H | H | H | Octyl |
| 213 | H | H | Methyl | H | Octyl |
| 214 | H | H | Butyl | H | Octyl |
| 215 | H | H | Hexyl | H | Octyl |
| 216 | H | H | 3-Methyl-2-butenyl | H | Octyl |
| 217 | H | H | Geranyl | H | Octyl |
| 218 | Methyl | Acetyl | Methyl | H | Ethyl |
| 219 | Methyl | Acetyl | Ethyl | H | Ethyl |
| 220 | Methyl | Acetyl | Butyl | H | Ethyl |
| 221 | Methyl | Acetyl | Hexyl | H | Ethyl |
| 222 | Methyl | Acetyl | 3-Methyl-2-butenyl | H | Ethyl |
| 223 | Methyl | Acetyl | Geranyl | H | Ethyl |
| 224 | Methyl | Acetyl | H | H | Ethyl |
| 225 | Methyl | Formyl | Methyl | H | Ethyl |
| 226 | Methyl | Formyl | Butyl | H | Ethyl |
| 227 | Methyl | Formyl | Hexyl | H | Ethyl |
| 228 | Methyl | Formyl | 3-Methyl-2-butenyl | H | Ethyl |
| 229 | Methyl | Formyl | Geranyl | H | Ethyl |
| 230 | Methyl | Formyl | H | H | Ethyl |
| 231 | Methyl | Methyl | Methyl | H | Ethyl |
| 232 | Methyl | Methyl | Butyl | H | Ethyl |
| 233 | Methyl | Methyl | Hexyl | H | Ethyl |
| 234 | Methyl | Methyl | 3-Methyl-2-butenyl | H | Ethyl |
| 235 | Methyl | Methyl | Geranyl | H | Ethyl |
| 236 | Methyl | Methyl | H | H | Ethyl |
| 237 | Methyl | Isopropyl | H | H | Ethyl |
| 238 | Methyl | Butyl | H | H | Ethyl |
| 239 | Methyl | Hexyl | H | H | Ethyl |
| 240 | Methyl | 2-Methyl-pentyl | H | H | Ethyl |

TABLE 7

| Compound No. | R₁ | R₂ | R₃ | R₄ | R₅ |
|---|---|---|---|---|---|
| 241 | Methyl | Octyl | H | H | Ethyl |
| 242 | Methyl | 2-Propenyl | H | H | Ethyl |
| 243 | Methyl | Geranyl | H | H | Ethyl |
| 244 | Methyl | H | Methyl | H | Ethyl |
| 245 | Methyl | H | Butyl | H | Ethyl |
| 246 | Methyl | H | Hexyl | H | Ethyl |
| 247 | Methyl | H | 3-Methyl-2-butenyl | H | Ethyl |
| 248 | Methyl | H | Geranyl | H | Ethyl |
| 249 | Methyl | H | H | H | Ethyl |
| 250 | Ethyl | Acetyl | Methyl | H | Butyl |
| 251 | Ethyl | Acetyl | Ethyl | H | Butyl |
| 252 | Ethyl | Acetyl | Butyl | H | Butyl |
| 253 | Ethyl | Acetyl | Hexyl | H | Butyl |
| 254 | Ethyl | Acetyl | 3-Methyl-2-butenyl | H | Butyl |
| 255 | Ethyl | Acetyl | Geranyl | H | Butyl |
| 256 | Ethyl | Acetyl | H | H | Butyl |
| 257 | Ethyl | Formyl | Methyl | H | Butyl |
| 258 | Ethyl | Formyl | Butyl | H | Butyl |
| 259 | Ethyl | Formyl | Hexyl | H | Butyl |
| 260 | Ethyl | Formyl | 3-Methyl-2-butenyl | H | Butyl |
| 261 | Ethyl | Formyl | Geranyl | H | Butyl |
| 262 | Ethyl | Formyl | H | H | Butyl |
| 263 | Ethyl | Methyl | Methyl | H | Butyl |
| 264 | Ethyl | Methyl | Butyl | H | Butyl |
| 265 | Ethyl | Methyl | Hexyl | H | Butyl |
| 266 | Ethyl | Methyl | 3-Methyl-2-butenyl | H | Butyl |
| 267 | Ethyl | Methyl | Geranyl | H | Butyl |
| 268 | Ethyl | Methyl | H | H | Butyl |
| 269 | Ethyl | Isopropyl | H | H | Butyl |
| 270 | Ethyl | Butyl | H | H | Butyl |
| 271 | Ethyl | Hexyl | H | H | Butyl |
| 272 | Ethyl | 2-Methyl-pentyl | H | H | Butyl |
| 273 | Ethyl | Octyl | H | H | Butyl |
| 274 | Ethyl | 2-Propenyl | H | H | Butyl |
| 275 | Ethyl | Geranyl | H | H | Butyl |
| 276 | Ethyl | H | Methyl | H | Butyl |
| 277 | Ethyl | H | Butyl | H | Butyl |
| 278 | Ethyl | H | Hexyl | H | Butyl |

TABLE 7-continued

| Compound No. | R₁ | R₂ | R₃ | R₄ | R₅ |
|---|---|---|---|---|---|
| 279 | Ethyl | H | 3-Methyl-2-butenyl | H | Butyl |
| 280 | Ethyl | H | Geranyl | H | Butyl |

TABLE 8

| Compound No. | R₁ | R₂ | R₃ | R₄ | R₅ |
|---|---|---|---|---|---|
| 281 | Ethyl | H | H | H | Butyl |
| 282 | Propyl | H | Methyl | H | Butyl |
| 283 | Propyl | H | Propyl | H | Butyl |
| 284 | Propyl | H | Butyl | H | Butyl |
| 285 | Propyl | H | Decyl | H | Butyl |
| 286 | Butyl | Acetyl | Methyl | H | Methyl |
| 287 | Butyl | Acetyl | Ethyl | H | Methyl |
| 288 | Butyl | Acetyl | Butyl | H | Methyl |
| 289 | Butyl | Acetyl | Hexyl | H | Methyl |
| 290 | Butyl | Acetyl | 3-Methyl-2-butenyl | H | Methyl |
| 291 | Butyl | Acetyl | Geranyl | H | Methyl |
| 292 | Butyl | Acetyl | H | H | Methyl |
| 293 | Butyl | Formyl | Methyl | H | Methyl |
| 294 | Butyl | Formyl | Butyl | H | Methyl |
| 295 | Butyl | Formyl | Hexyl | H | Methyl |
| 296 | Butyl | Formyl | 3-Methyl-2-butenyl | H | Methyl |
| 297 | Butyl | Formyl | Geranyl | H | Methyl |
| 298 | Butyl | Formyl | H | H | Methyl |
| 299 | Butyl | Methyl | Methyl | H | Methyl |
| 300 | Butyl | Methyl | Butyl | H | Methyl |
| 301 | Butyl | Methyl | H | Methyl | Methyl |
| 302 | Butyl | Isopropyl | H | Methyl | Methyl |
| 303 | Butyl | Butyl | H | Methyl | Methyl |
| 304 | Butyl | Hexyl | H | Methyl | Methyl |
| 305 | Butyl | 2-Methyl-pentyl | H | Methyl | Methyl |
| 306 | Butyl | Octyl | H | Methyl | Methyl |
| 307 | Butyl | 2-Propenyl | H | Methyl | Methyl |
| 308 | Butyl | Geranyl | H | Methyl | Methyl |
| 309 | Butyl | H | Methyl | Methyl | Methyl |
| 310 | Butyl | H | Butyl | Methyl | Methyl |
| 311 | Butyl | H | Hexyl | Methyl | Methyl |
| 312 | Butyl | H | 3-Methyl-2-butenyl | Methyl | Methyl |
| 313 | Butyl | H | Geranyl | Methyl | Methyl |
| 314 | Butyl | H | H | Methyl | Methyl |
| 315 | Hexyl | Acetyl | Methyl | H | Ethyl |
| 316 | Hexyl | Acetyl | Ethyl | H | Ethyl |
| 317 | Hexyl | Acetyl | Butyl | H | Ethyl |
| 318 | Hexyl | Acetyl | Hexyl | H | Ethyl |
| 319 | Hexyl | Acetyl | 3-Methyl-2-butenyl | H | Ethyl |
| 320 | Hexyl | Acetyl | Geranyl | H | Ethyl |

TABLE 9

| Compound No. | R₁ | R₂ | R₃ | R₄ | R₅ |
|---|---|---|---|---|---|
| 321 | Hexyl | Acetyl | H | H | Ethyl |
| 322 | Hexyl | Formyl | Methyl | H | Ethyl |
| 323 | Hexyl | Formyl | Butyl | H | Ethyl |
| 324 | Hexyl | Formyl | Hexyl | H | Ethyl |
| 325 | Hexyl | Formyl | 3-Methyl-2-butenyl | H | Ethyl |
| 326 | Hexyl | Formyl | Geranyl | H | Ethyl |
| 327 | Hexyl | Formyl | H | H | Ethyl |
| 328 | Hexyl | Methyl | Methyl | H | Ethyl |
| 329 | Hexyl | Methyl | Butyl | H | Ethyl |
| 330 | Hexyl | Methyl | H | H | Ethyl |
| 331 | Hexyl | Isopropyl | H | H | Ethyl |
| 332 | Hexyl | Butyl | H | H | Ethyl |
| 333 | Hexyl | Hexyl | H | H | Ethyl |
| 334 | Hexyl | 2-Methyl-pentyl | H | H | Ethyl |
| 335 | Hexyl | Octyl | H | H | Ethyl |
| 336 | Hexyl | 2-Propenyl | H | H | Ethyl |

TABLE 9-continued

| Compound No. | R$_1$ | R$_2$ | R$_3$ | R$_4$ | R$_5$ |
|---|---|---|---|---|---|
| 337 | Hexyl | Geranyl | H | H | Ethyl |
| 338 | Hexyl | H | Methyl | H | Ethyl |
| 339 | Hexyl | H | Butyl | H | Ethyl |
| 340 | Hexyl | H | Hexyl | H | Ethyl |
| 341 | Hexyl | H | 3-Methyl-2-butenyl | H | Ethyl |
| 342 | Hexyl | H | Geranyl | H | Ethyl |
| 343 | Hexyl | H | H | H | Ethyl |
| 344 | Octyl | Acetyl | Methyl | H | Ethyl |
| 345 | Octyl | Acetyl | Ethyl | H | Ethyl |
| 346 | Octyl | Acetyl | Butyl | H | Ethyl |
| 347 | Octyl | Acetyl | Hexyl | H | Ethyl |
| 348 | Octyl | Acetyl | 3-Methyl-2-butenyl | H | Ethyl |
| 349 | Octyl | Acetyl | Geranyl | H | Ethyl |
| 350 | Octyl | Acetyl | H | H | Ethyl |
| 351 | Octyl | Formyl | Methyl | H | Ethyl |
| 352 | Octyl | Formyl | Butyl | H | Ethyl |
| 353 | Octyl | Formyl | Hexyl | H | Ethyl |
| 354 | Octyl | Formyl | 3-Methyl-2-butenyl | H | Ethyl |
| 355 | Octyl | Formyl | Geranyl | H | Ethyl |
| 356 | Octyl | Formyl | H | H | Ethyl |
| 357 | Octyl | Methyl | Methyl | H | Ethyl |
| 358 | Octyl | Methyl | Butyl | H | Ethyl |
| 359 | Octyl | Methyl | H | H | Ethyl |
| 360 | Octyl | Isopropyl | H | H | Ethyl |

TABLE 10

| Compound No. | R$_1$ | R$_2$ | R$_3$ | R$_4$ | R$_5$ |
|---|---|---|---|---|---|
| 361 | Octyl | Butyl | H | H | Ethyl |
| 362 | Octyl | Hexyl | H | H | Ethyl |
| 363 | Octyl | 2-Methyl-pentyl | H | H | Ethyl |
| 364 | Octyl | Octyl | H | H | Ethyl |
| 365 | Octyl | 2-Propenyl | H | H | Ethyl |
| 366 | Octyl | Geranyl | H | H | Ethyl |
| 367 | Octyl | H | Methyl | H | Ethyl |
| 368 | Octyl | H | Butyl | H | Ethyl |
| 369 | Octyl | H | Hexyl | H | Ethyl |
| 370 | Octyl | H | 3-Methyl-2-butenyl | H | Ethyl |
| 371 | Octyl | H | Geranyl | H | Ethyl |
| 372 | Octyl | H | H | H | Ethyl |
| 373 | Methyl | Acetyl | Methyl | Acetyl | Ethyl |
| 374 | Methyl | Acetyl | Ethyl | Acetyl | Ethyl |
| 375 | Methyl | Acetyl | Butyl | Acetyl | Ethyl |
| 376 | Methyl | Acetyl | Hexyl | Acetyl | Ethyl |
| 377 | Methyl | Acetyl | 3-Methyl-2-butenyl | Acetyl | Ethyl |
| 378 | Methyl | Acetyl | Geranyl | Acetyl | Ethyl |
| 379 | Methyl | Acetyl | H | Acetyl | Ethyl |
| 380 | Methyl | Formyl | Methyl | Acetyl | Ethyl |
| 381 | Methyl | Formyl | Butyl | Acetyl | Ethyl |
| 382 | Methyl | Formyl | Hexyl | Acetyl | Ethyl |
| 383 | Methyl | Formyl | 3-Methyl-2-butenyl | Acetyl | Ethyl |
| 384 | Methyl | Formyl | Geranyl | Acetyl | Ethyl |
| 385 | Methyl | Formyl | H | Acetyl | Ethyl |
| 386 | Methyl | Methyl | Methyl | H | Acetyl |
| 387 | Methyl | Methyl | Butyl | H | Acetyl |
| 388 | Methyl | Methyl | Hexyl | H | Acetyl |
| 389 | Methyl | Methyl | 3-Methyl-2-butenyl | H | Acetyl |
| 390 | Methyl | Methyl | Geranyl | H | Acetyl |
| 391 | Methyl | Methyl | H | H | Acetyl |
| 392 | Methyl | Isopropyl | H | H | Acetyl |
| 393 | Methyl | Butyl | H | H | Acetyl |
| 394 | Methyl | Hexyl | H | H | Acetyl |
| 395 | Methyl | 2-Methyl-pentyl | H | H | Acetyl |
| 396 | Methyl | Octyl | H | H | Acetyl |
| 397 | Methyl | 2-Propenyl | H | H | Acetyl |
| 398 | Methyl | Geranyl | H | H | Acetyl |
| 399 | Methyl | H | Methyl | H | Acetyl |
| 400 | Methyl | H | Butyl | H | Acetyl |

TABLE 11

| Compound No. | R$_1$ | R$_2$ | R$_3$ | R$_4$ | R$_5$ |
|---|---|---|---|---|---|
| 401 | Methyl | H | Hexyl | H | Acetyl |
| 402 | Methyl | H | 3-Methyl-2-butenyl | H | Acetyl |
| 403 | Methyl | H | Geranyl | H | Acetyl |
| 404 | Methyl | H | H | H | Acetyl |
| 405 | Ethyl | Acetyl | Methyl | H | Acetyl |
| 406 | Ethyl | Acetyl | Ethyl | H | Acetyl |
| 407 | Ethyl | Acetyl | Butyl | H | Acetyl |
| 408 | Ethyl | Acetyl | Hexyl | H | Acetyl |
| 409 | Ethyl | Acetyl | 3-Methyl-2-butenyl | H | Acetyl |
| 410 | Ethyl | Acetyl | Geranyl | H | Acetyl |
| 411 | Ethyl | Acetyl | H | H | Acetyl |
| 412 | Ethyl | Formyl | Methyl | H | Acetyl |
| 413 | Ethyl | Formyl | Butyl | H | Acetyl |
| 414 | Ethyl | Formyl | Hexyl | H | Acetyl |
| 415 | Ethyl | Formyl | 3-Methyl-2-butenyl | H | Acetyl |
| 416 | Ethyl | Formyl | Geranyl | H | Acetyl |
| 417 | Ethyl | Formyl | H | H | Acetyl |
| 418 | Ethyl | Methyl | Methyl | H | Acetyl |
| 419 | Ethyl | Methyl | Butyl | H | Acetyl |
| 420 | Ethyl | Methyl | Hexyl | H | Acetyl |
| 421 | Ethyl | Methyl | 3-Methyl-2-butenyl | H | Acetyl |
| 422 | Ethyl | Methyl | Geranyl | H | Acetyl |
| 423 | Ethyl | Methyl | H | H | Acetyl |
| 424 | Ethyl | Isopropyl | H | H | Acetyl |
| 425 | Ethyl | Butyl | H | H | Acetyl |
| 426 | Ethyl | Hexyl | H | H | Acetyl |
| 427 | Ethyl | 2-Methyl-pentyl | H | H | Acetyl |
| 428 | Ethyl | Octyl | H | H | Acetyl |
| 429 | Ethyl | 2-Propenyl | H | H | Acetyl |
| 430 | Ethyl | Geranyl | H | H | Acetyl |
| 431 | Ethyl | H | Methyl | H | Acetyl |
| 432 | Ethyl | H | Butyl | H | Acetyl |
| 433 | Ethyl | H | Hexyl | H | Acetyl |
| 434 | Ethyl | H | 3-Methyl-2-butenyl | H | Acetyl |
| 435 | Ethyl | H | Geranyl | H | Acetyl |
| 436 | Ethyl | H | H | H | Acetyl |
| 437 | Propyl | H | Methyl | H | Acetyl |
| 438 | Propyl | H | Propyl | H | Acetyl |
| 439 | Propyl | H | Butyl | H | Acetyl |
| 440 | Propyl | H | Decyl | H | Acetyl |

TABLE 12

| Compound No. | R$_1$ | R$_2$ | R$_3$ | R$_4$ | R$_5$ |
|---|---|---|---|---|---|
| 441 | Butyl | Acetyl | Methyl | H | Formyl |
| 442 | Butyl | Acetyl | Ethyl | H | Formyl |
| 443 | Butyl | Acetyl | Butyl | H | Formyl |
| 444 | Butyl | Acetyl | Hexyl | H | Formyl |
| 445 | Butyl | Acetyl | 3-Methyl-2-butenyl | H | Formyl |
| 446 | Butyl | Acetyl | Geranyl | H | Formyl |
| 447 | Butyl | Acetyl | H | H | Formyl |
| 448 | Butyl | Formyl | Methyl | H | Formyl |
| 449 | Butyl | Formyl | Butyl | H | Formyl |
| 450 | Butyl | Formyl | Hexyl | H | Formyl |
| 451 | Butyl | Formyl | 3-Methyl-2-butenyl | H | Formyl |
| 452 | Butyl | Formyl | Geranyl | H | Formyl |
| 453 | Butyl | Formyl | H | H | Formyl |
| 454 | Butyl | Methyl | Methyl | H | Formyl |
| 455 | Butyl | Methyl | Butyl | H | Formyl |
| 456 | Butyl | Methyl | H | H | Formyl |
| 457 | Butyl | Isopropyl | H | H | Formyl |
| 458 | Butyl | Butyl | H | H | Formyl |
| 459 | Butyl | Hexyl | H | H | Formyl |
| 460 | Butyl | 2-Methyl-pentyl | H | H | Formyl |
| 461 | Butyl | Octyl | H | H | Formyl |
| 462 | Butyl | 2-Propenyl | H | H | Formyl |
| 463 | Butyl | Geranyl | H | H | Formyl |
| 464 | Butyl | H | Methyl | H | Formyl |
| 465 | Butyl | H | Butyl | H | Formyl |

TABLE 12-continued

| Compound No. | $R_1$ | $R_2$ | $R_3$ | $R_4$ | $R_5$ |
|---|---|---|---|---|---|
| 466 | Butyl | H | Hexyl | H | Formyl |
| 467 | Butyl | H | 3-Methyl-2-butenyl | H | Formyl |
| 468 | Butyl | H | Geranyl | H | Formyl |
| 469 | Butyl | H | H | H | Formyl |
| 470 | Hexyl | Acetyl | Methyl | H | Propionyl |
| 471 | Hexyl | Acetyl | Ethyl | H | Propionyl |
| 472 | Hexyl | Acetyl | Butyl | H | Propionyl |
| 473 | Hexyl | Acetyl | Hexyl | H | Propionyl |
| 474 | Hexyl | Acetyl | 3-Methyl-2-butenyl | H | Propionyl |
| 475 | Hexyl | Acetyl | Geranyl | H | Propionyl |
| 476 | Hexyl | Acetyl | H | H | Propionyl |
| 477 | Hexyl | Formyl | Methyl | H | Propionyl |
| 478 | Hexyl | Formyl | Butyl | H | Propionyl |
| 479 | Hexyl | Formyl | Hexyl | H | Propionyl |
| 480 | Hexyl | Formyl | 3-Methyl-2-butenyl | H | Propionyl |

TABLE 13

| Compound No. | $R_1$ | $R_2$ | $R_3$ | $R_4$ | $R_5$ |
|---|---|---|---|---|---|
| 481 | Hexyl | Formyl | Geranyl | H | Propionyl |
| 482 | Hexyl | Formyl | H | H | Propionyl |
| 483 | Hexyl | Methyl | Methyl | H | Propionyl |
| 484 | Hexyl | Methyl | Butyl | H | Propionyl |
| 485 | Hexyl | Methyl | H | H | Propionyl |
| 486 | Hexyl | Isopropyl | H | H | Propionyl |
| 487 | Hexyl | Butyl | H | H | Propionyl |
| 488 | Hexyl | Hexyl | H | H | Propionyl |
| 489 | Hexyl | 2-Methyl-pentyl | H | H | Propionyl |
| 490 | Hexyl | Octyl | H | H | Propionyl |
| 491 | Hexyl | 2-Propenyl | H | H | Propionyl |
| 492 | Hexyl | Geranyl | H | H | Propionyl |
| 493 | Hexyl | H | Methyl | H | Propionyl |
| 494 | Hexyl | H | Butyl | H | Propionyl |
| 495 | Hexyl | H | Hexyl | H | Propionyl |
| 496 | Hexyl | H | 3-Methyl-2-butenyl | H | Propionyl |
| 497 | Hexyl | H | Geranyl | H | Propionyl |
| 498 | Hexyl | H | H | H | Propionyl |
| 499 | Octyl | Acetyl | Methyl | H | Propionyl |
| 500 | Octyl | Acetyl | Ethyl | H | Benzoyl |
| 501 | Octyl | Acetyl | Butyl | H | Benzoyl |
| 502 | Octyl | Acetyl | Hexyl | H | Benzoyl |
| 503 | Octyl | Acetyl | 3-Methyl-2-butenyl | H | Benzoyl |
| 504 | Octyl | Acetyl | Geranyl | H | Benzoyl |
| 505 | Octyl | Acetyl | H | H | Benzoyl |
| 506 | Octyl | Formyl | Methyl | H | Benzoyl |
| 507 | Octyl | Formyl | Butyl | H | Benzoyl |
| 508 | Octyl | Formyl | Hexyl | H | Benzoyl |
| 509 | Octyl | Formyl | 3-Methyl-2-butenyl | H | Benzoyl |
| 510 | Octyl | Formyl | Geranyl | H | Benzoyl |
| 511 | Octyl | Formyl | H | H | Benzoyl |
| 512 | Octyl | Methyl | Methyl | H | Benzoyl |
| 513 | Octyl | Methyl | Butyl | H | Benzoyl |
| 514 | Methyl | Methyl | H | H | Benzoyl |
| 515 | Methyl | Isopropyl | H | H | Benzoyl |
| 516 | Methyl | Butyl | H | H | Benzoyl |
| 517 | Methyl | Hexyl | H | H | Benzoyl |
| 518 | Methyl | 2-Methyl-pentyl | H | H | Benzoyl |
| 519 | Methyl | Octyl | H | H | Benzoyl |
| 520 | Methyl | 2-Propenyl | H | H | Benzoyl |

TABLE 14

| Compound No. | $R_1$ | $R_2$ | $R_3$ | $R_4$ | $R_5$ |
|---|---|---|---|---|---|
| 521 | Methyl | Geranyl | H | H | Benzoyl |
| 522 | Butyl | H | Methyl | H | Benzoyl |
| 523 | Butyl | H | Butyl | H | Benzoyl |
| 524 | Butyl | H | Hexyl | H | Benzoyl |
| 525 | Butyl | H | 3-Methyl-2-butenyl | H | Benzoyl |
| 526 | Butyl | H | Geranyl | H | Benzoyl |
| 527 | Butyl | H | H | H | Benzoyl |
| 528 | Methyl | Acetyl | Methyl | H | Cinnamoyl |
| 529 | Methyl | Acetyl | Ethyl | H | Cinnamoyl |
| 530 | Methyl | Acetyl | Butyl | H | Cinnamoyl |
| 531 | Methyl | Acetyl | Hexyl | H | Cinnamoyl |
| 532 | Methyl | Acetyl | 3-Methyl-2-butenyl | H | Cinnamoyl |
| 533 | Methyl | Acetyl | Geranyl | H | Cinnamoyl |
| 534 | Methyl | Acetyl | H | H | Cinnamoyl |
| 535 | Methyl | H | Methyl | H | Cinnamoyl |
| 536 | Methyl | H | Butyl | H | Cinnamoyl |
| 537 | Methyl | H | Hexyl | H | Cinnamoyl |
| 538 | Methyl | H | 3-Methyl-2-butenyl | H | Cinnamoyl |
| 539 | Methyl | H | Geranyl | H | Cinnamoyl |
| 540 | Methyl | H | H | H | Cinnamoyl |
| 541 | Methyl | Methyl | Methyl | H | 3,5-Dimethoxy-4-hydroxycinnamoyl |
| 542 | Methyl | Methyl | Butyl | H | 3,5-Dimethoxy-4-hydroxycinnamoyl |
| 543 | Methyl | Methyl | Hexyl | H | 3,5-Dimethoxy-4-hydroxycinnamoyl |
| 544 | Methyl | Methyl | 3-Methyl-2-butenyl | H | 3,5-Dimethoxy-4-hydroxycinnamoyl |
| 545 | Methyl | Methyl | Geranyl | H | 3,5-Dimethoxy-4-hydroxycinnamoyl |
| 546 | Methyl | Methyl | H | H | 3,5-Dimethoxy-4-hydroxycinnamoyl |
| 547 | Methyl | Isopropyl | H | H | 3,5-Dimethoxy-4-hydroxycinnamoyl |
| 548 | Methyl | Butyl | H | H | 3,5-Dimethoxy-4-hydroxycinnamoyl |
| 549 | Methyl | Hexyl | H | H | 3,5-Dimethoxy-4-hydroxycinnamoyl |
| 550 | Methyl | 2-Methyl-pentyl | H | H | 3,5-Dimethoxy-4-hydroxycinnamoyl |

TABLE 15

| Compound No. | $R_1$ | $R_2$ | $R_3$ | $R_4$ | $R_5$ |
|---|---|---|---|---|---|
| 551 | Methyl | Octyl | H | H | 3,5-Dimethoxy-4-hydroxycinnamoyl |
| 552 | Methyl | 2-Propenyl | H | H | 3,5-Dimethoxy-4-hydroxycinnamoyl |
| 553 | Methyl | Geranyl | H | H | 3,5-Dimethoxy-4-hydroxycinnamoyl |
| 554 | Methyl | H | Methyl | H | 3,5-Dimethoxy-4-hydroxycinnamoyl |
| 555 | Methyl | H | Butyl | H | 3,5-Dimethoxy-4-hydroxycinnamoyl |
| 556 | Methyl | H | Hexyl | H | 3,5-Dimethoxy-4-hydroxycinnamoyl |
| 557 | Methyl | H | 3-Methyl-2-butenyl | H | 3,5-Dimethoxy-4-hydroxycinnamoyl |
| 558 | Methyl | H | Geranyl | H | 3,5-Dimethoxy-4-hydroxycinnamoyl |
| 559 | Methyl | H | H | H | 3,5-Dimethoxy-4-hydroxycinnamoyl |
| 560 | Ethyl | Acetyl | Methyl | H | 4-Hydroxy-3-methoxycinnamoyl |
| 561 | Ethyl | Acetyl | Ethyl | H | 4-Hydroxy-3-methoxycinnamoyl |

TABLE 15-continued

| Compound No. | R₁ | R₂ | R₃ | R₄ | R₅ |
|---|---|---|---|---|---|
| 562 | Ethyl | Acetyl | Butyl | H | 4-Hydroxy-3-methoxycinnamoyl |
| 563 | Ethyl | Acetyl | Hexyl | H | 4-Hydroxy-3-methoxycinnamoyl |
| 564 | Ethyl | Acetyl | 3-Methyl-2-butenyl | H | 4-Hydroxy-3-methoxycinnamoyl |
| 565 | Ethyl | Acetyl | Geranyl | H | 4-Hydroxy-3-methoxycinnamoyl |
| 566 | Ethyl | Acetyl | H | H | 4-Hydroxy-3-methoxycinnamoyl |
| 567 | Ethyl | Formyl | Methyl | H | 4-Hydroxy-3-methoxycinnamoyl |
| 568 | Ethyl | Formyl | Butyl | H | 4-Hydroxy-3-methoxycinnamoyl |
| 569 | Ethyl | Formyl | Hexyl | H | 4-Hydroxy-3-methoxycinnamoyl |
| 570 | Ethyl | Formyl | 3-Methyl-2-butenyl | H | 4-Hydroxy-3-methoxycinnamoyl |

TABLE 16

| Compound No. | R₁ | R₂ | R₃ | R₄ | R₅ |
|---|---|---|---|---|---|
| 571 | Ethyl | Formyl | Geranyl | H | 4-Hydroxy-3-methoxycinnamoyl |
| 572 | Ethyl | Formyl | H | H | 4-Hydroxy-3-methoxycinnamoyl |
| 573 | Methyl | Methyl | Methyl | H | 4-Hydroxy-3-methoxycinnamoyl |
| 574 | Methyl | Methyl | Butyl | H | 4-Hydroxy-3-methoxycinnamoyl |
| 575 | Methyl | Methyl | Hexyl | H | 4-Hydroxy-3-methoxycinnamoyl |
| 576 | Methyl | Methyl | 3-Methyl-2-butenyl | H | 4-Hydroxy-3-methoxycinnamoyl |
| 577 | Methyl | Methyl | Geranyl | H | 4-Hydroxy-3-methoxycinnamoyl |
| 578 | Methyl | Methyl | H | H | 4-Hydroxy-3-methoxycinnamoyl |
| 579 | Methyl | Isopropyl | H | H | 4-Hydroxy-3-methoxycinnamoyl |
| 580 | Methyl | Butyl | H | H | 4-Hydroxy-3-methoxycinnamoyl |
| 581 | Methyl | Hexyl | H | H | 4-Hydroxy-3-methoxycinnamoyl |
| 582 | Methyl | 2-Methyl-pentyl | H | H | 4-Hydroxy-3-methoxycinnamoyl |
| 583 | Methyl | Octyl | H | H | 4-Hydroxy-3-methoxycinnamoyl |
| 584 | Methyl | 2-Propenyl | H | H | 4-Hydroxy-3-methoxycinnamoyl |
| 585 | Methyl | Geranyl | H | H | 4-Hydroxy-3-methoxycinnamoyl |
| 586 | Methyl | H | Methyl | H | Benzyl |
| 587 | Methyl | H | Butyl | H | Benzyl |
| 588 | Methyl | H | Hexyl | H | Benzyl |
| 589 | Methyl | H | 3-Methyl-2-butenyl | H | Benzyl |
| 590 | Methyl | H | Geranyl | H | Benzyl |
| 591 | Methyl | H | H | H | Benzyl |
| 592 | Propyl | H | Methyl | H | Benzyl |
| 593 | Propyl | H | Propyl | H | Benzyl |
| 594 | Propyl | H | Butyl | H | Benzyl |
| 595 | Propyl | H | Decyl | H | Benzyl |

TABLE 17

| Compound No. | R₁ | R₂ | R₃ | R₄ | R₅ |
|---|---|---|---|---|---|
| 596 | Methyl | Methyl | H | H | 2-Propenyl |
| 597 | Methyl | Isopropyl | H | H | 2-Propenyl |
| 598 | Methyl | Butyl | H | H | 2-Propenyl |
| 599 | Methyl | Hexyl | H | H | 2-Propenyl |
| 600 | Methyl | 2-Methyl-pentyl | H | H | 2-Propenyl |
| 601 | Methyl | Octyl | H | H | 2-Propenyl |
| 602 | Methyl | 2-Propenyl | H | H | 2-Propenyl |
| 603 | Methyl | Geranyl | H | H | 2-Propenyl |
| 604 | Methyl | H | Methyl | H | 2-Propenyl |
| 605 | Methyl | H | Butyl | H | 2-Propenyl |
| 606 | Methyl | H | Hexyl | H | 2-Propenyl |
| 607 | Methyl | H | 3-Methyl-2-butenyl | H | 2-Propenyl |
| 608 | Methyl | H | Geranyl | H | 2-Propenyl |
| 609 | Methyl | H | H | H | 2-Propenyl |
| 610 | Methyl | H | Methyl | H | 2-Propenyl |
| 611 | Methyl | H | Propyl | H | 2-Propenyl |
| 612 | Methyl | H | Butyl | H | 2-Propenyl |
| 613 | Methyl | H | Decyl | H | 2-Propenyl |
| 614 | Methyl | Methyl | H | H | Geranyl |
| 615 | Methyl | Isopropyl | H | H | Geranyl |
| 616 | Methyl | Butyl | H | H | Geranyl |
| 617 | Methyl | Hexyl | H | H | Geranyl |
| 618 | Methyl | 2-Methyl-pentyl | H | H | Geranyl |
| 619 | Methyl | Octyl | H | H | Geranyl |
| 620 | Methyl | 2-Propenyl | H | H | Geranyl |
| 621 | Methyl | Geranyl | H | H | Geranyl |
| 622 | Methyl | H | Methyl | H | Geranyl |
| 623 | Methyl | H | Butyl | H | Geranyl |
| 624 | Methyl | H | Hexyl | H | Geranyl |
| 625 | Methyl | H | 3-Methyl-2-butenyl | H | Geranyl |
| 626 | Methyl | H | Geranyl | H | Geranyl |
| 627 | Methyl | H | H | H | Geranyl |
| 628 | Methyl | H | Methyl | H | Geranyl |
| 629 | Methyl | H | Propyl | H | Geranyl |
| 630 | Methyl | H | Butyl | H | Geranyl |

In the present invention, physiologically acceptable salts of these compounds are also included. As used herein, physiologically acceptable salts refer to alkali addition salts having no toxicity with respect to compounds having a hydroxyl group, especially compounds having a hydroxyl group at the 3- and/or 4-positions among the above-described compounds, and examples thereof include nontoxic salts such as sodium salt, potassium salt, magnesium salt, calcium salt, ammonium salt and nontoxic amine salt. These salts can be prepared by a conventionally known method.

With respect to the compound having no hydroxyl group, there can be exemplified nontoxic addition salts prepared by reacting an amino group of an aromatic ring with mineral acids such as hydrochloric acid, sulfuric acid and phosphoric acid, or various organic acids such as acetic acid, propionic acid, succinic acid, tartaric acid, maleic acid and fumaric acid, or sulfonic acids such as methanesulfonic acid. These salts can be prepared by a conventionally known method.

As described in the examples described hereinafter, the 7-aminoquinolinone derivative and its physiologically acceptable salt thereof in the present invention have low toxicity and are extremely useful as a therapeutic agent for chronic obstructive pulmonary disease for treating or preventing various chronic obstructive pulmonary diseases.

Chronic obstructive pulmonary disease as used herein refers to lung diseases including chronic bronchitis and pulmonary emphysema. Chronic obstructive pulmonary disease is generally characterized by progressive and irreversible airflow limitation. In many cases, it is accompanied by airway hyper-responsiveness and some chronic obstructive pulmonary disease is reversible symptom. Chronic bronchitis is characterized by chronic moist cough for 3 or more consecutive months in each of consecutive 2 years. Pulmonary emphysema is an permanent abnormal swelling of alveoli distal to terminal bronchiole, which is accompanied by destructive changes of pulmonary alveolus walls and having no obvious fibrosis. Destructive change is defined as irregular swelling of respiratory air spaces, wherein regular appearances of pulmonary acinuses and its components may be destroyed and disappeared.

As described above, chronic obstructive pulmonary disease is characterized by irreversible airflow limitation and has a pathologic characteristic different from asthma, which is a reversible airflow limitation. Furthermore, in international asthma therapy guideline, "Guideline for the Diagnosis and Management of Asthma (NHLBI, 2002)", inhalation steroids for drug treatment against bronchial asthma are recommended as a first choice and its excellent effectiveness is confirmed. However, in the similar global guideline, Global initiative for chronic obstructive lung disease (GOLD; NHLBI/WHO, 2001), the effect of steroids on chronic obstructive pulmonary disease is a little and therefore its use is not recommended well. Thus, chronic obstructive pulmonary disease and bronchial asthma have different responses to drugs.

Main therapy for chronic obstructive pulmonary disease is use of bronchodilator such as anticholinergic agents and β-receptor agonists, wherein a symptomatic therapy for relaxing temporarily airway obstructive state is carried out. Recently, research and development of a long-acting anticholinergic agent and β receptor agonist has been carried out, but any of them belongs to a symptomatic therapy. The risk factor of chronic obstructive pulmonary disease is noxious micro particles due to smoking and air pollution. It is believed that lasting chronic inflammation state in peripheral respiratory tract and pulmonary alveoli due to long-term exposure of them is the cause for the disease development. That is, the above mentioned GOLD describes clearly that there is observed neutrophilic inflammation in a lung and that important one as its causal and progressive factor is inflammation due to imbalance between a protease and a protease inhibitor, and oxidative stress. However, any agents capable of treating chronic obstructive pulmonary disease by suppressing such inflammation have never been marketed.

The present inventors have paid attention to airway inflammation due to oxidative stress, which is considered to as an important factor for the onset of chronic obstructive pulmonary disease, made an animal model corresponding to chronic obstructive pulmonary disease and intensively studied about a drug capable of treating airway inflammation in the model. Consequently, they have found a compound which exerts a potent therapeutic effect in a model in which the airway is exposed to peroxynitrite, a potent oxidant produced in the body described in GOLD, to induce airway hyper-responsiveness.

It is suggested that chronic obstructive pulmonary disease is also involved in air pollution substances and it is known that, when exposing animals such as rat and guinea pig to ozone, one of air pollution substances, airway inflammation, including airway hyper-responsiveness, similar to chronic obstructive pulmonary disease is induced. Therefore, the present inventors have investigated effectiveness of the compounds of the present invention against a test model in which airway hyper-responsiveness is induced by exposure of ozone to guinea pig, and thus obtaining such a finding that the compounds of the present invention have equal or greater effectiveness than that of the conventional agents and are therefore extremely useful as a agent for chronic obstructive pulmonary disease.

The therapeutic agent for chronic obstructive pulmonary disease of the present invention can be administered orally (taken internally or inhaled) or parenterally (e.g., intravenous administration, subcutaneous administration, transcutaneous administration or intrarectal administration), and can be prepared into a formulation form suitable for the respective administration method at the time of administration.

The formulation can be prepared in various formulation forms such as tablets, capsules, granules, grains, powders, troches, sublingual formulations, suppositories, ointments, injections, emulsions, suspensions and syrups according to the specific application.

When preparing these formulations, said formulations can be formulated in accordance with known methods using nontoxic additives normally used in this type of formulation, examples of which include vehicles, binders, disintegration agents, lubricants, preservatives, antioxidants, isotonic agents, buffers, coating agents, correctives, dissolving assistants, bases, dispersants, stabilizers and colorants. Specific examples of these nontoxic additives are listed below.

Examples of vehicles include starch and its derivatives (such as dextrin and carboxymethyl starch), cellulose and its derivatives (such as methyl cellulose and hydroxypropyl cellulose), saccharides (such as lactose, refined sugar and glucose), silicic acid and silicates (such as naturally-occurring aluminum silicate and magnesium silicate), carbonates (such as calcium carbonate, magnesium carbonate, and sodium hydrogen carbonate), aluminum-magnesium hydroxide, synthetic hydrotalcite, polyoxythylene derivatives, glycerin monostearate and sorbitan monooleate.

Examples of binders include starch and its derivatives (such as pregelatinized starch and dextrin), cellulose and its derivatives (such as ethyl cellulose, sodium carboxymethyl cellulose and hydroxypropylmethyl cellulose), gum arabic, tragacanth gum, gelatin, saccharides (such as glucose and refined sugar), ethanol and polyvinyl alcohol.

Examples of disintegration agents include starch and its derivatives (such as carboxymethyl starch and hydroxypropyl starch), cellulose and its derivatives (such as sodium carboxymethyl cellulose, crystal cellulose and hydroxypropylmethyl cellulose), carbonates (such as calcium carbonate and calcium hydrogen carbonate), tragacanth gum, gelatin and agar.

Examples of lubricants include stearic acid, calcium stearate, magnesium stearate, talc, silicic acid and its salts (such as light silicic anhydride and naturally-occurring aluminum silicate), titanium oxide, calcium hydrogen phosphate, dry aluminum hydroxide gel and macrogall.

Examples of preservatives include paraoxybenzoate esters, sulfites (such as sodium sulfite and sodium pyrosulfite), phosphates (such as sodium phosphate, calcium polyphosphate, sodium polyphosphate and sodium metaphosphate), alcohols (such as chlorobutanol and benzyl alcohol), benzalkonium chloride, benzetonium chloride, phenol, cresol, chlorocresol, dehydroacetic acid, sodium dehydroacetate, glycerin sorbate and saccharides.

Examples of antioxidants include sulfites (such as sodium sulfite and sodium hydrogen sulfite), rongalite, erysorbic acid, L-ascorbic acid, cysteine thioglycerol, butylhydroxy anisole, dibutylhydroxy toluene, propyl gallate, ascorbic palmitate and dl-α-tocopherol.

Examples of isotonic agents include sodium chloride, sodium nitrate, potassium nitrate, dextrin, glycerin and glucose. In addition, examples of buffers include sodium carbonate, hydrochloric acid, boric acid and phosphates (such as sodium hydrogen phosphate).

Examples of coating agents include cellulose derivatives (such as hydroxypropyl cellulose, cellulose acetophthalate and hydroxypropyl methyl cellulose phthalate), shellac, polyvinyl pyrrolidone, polyvinyl pyridines (such as poly-2-vinylpyridine and poly-2-vinyl-5-ethylpyridine), polyvinylacetyldiethylaminoacetate, polyvinyl alcohol phthalate and methacrylate-methacrylic acid copolymer.

Examples of correctives include saccharides (such as glucose, refined sugar and lactose), sodium saccharine and sugar-alcohols. Examples of dissolving assistants include ethylenediamine, nicotinic amide, sodium saccharine, citric acid, citrates, sodium benzoate, soaps, polyvinyl pyrrolidone, polysorbates, sorbitan fatty acid esters, glycerin, polypropylene glycol and benzyl alcohol.

Examples of bases include fats (such as lard), vegetable oils (such as olive oil and sesame oil), animal oils, lanolinic acid, vaseline, paraffin, wax, resin, bentonite, glycerin, glycolic oil and higher alcohols (such as stearyl alcohol and cetanol).

Examples of dispersants include gum arabic, tragacanth gum, cellulose derivatives (such as methyl cellulose), stearate polyesters, sorbitan sesquioleates, aluminum monostearate, sodium alginate, polysorbates and sorbitan fatty acid esters. In addition, examples of stabilizers include sulfites (such as sodium bisulfite), nitrogen and carbon dioxide.

In addition, although the content of the 7-aminoquinolinone derivative and its physiologically acceptable salt thereof in this formulation varies according to the formulation form. In general, it is preferably contained at the concentration of 0.01 to 100% by weight.

Although the dose of the therapeutic agent for chronic obstructive pulmonary disease of the present invention can be varied over a wide range according to the target species of warm-blooded animal including humans, the severity of the symptoms and the diagnosis of a physician. In general, in the case of oral administration, the dose as the amount of active ingredient is from 0.01 to 50 mg, and preferably from 0.05 to 10 mg, per day per 1 kg of body weight.

In the case of parenteral administration, the dose as the amount of active ingredient is from 0.01 to 10 mg, and preferably from 0.01 to 5 mg, per day per 1 kg of body weight. In addition, the above dose can be administered in a single administration or divided into several administrations, and can be suitably varied according to the severity of patient symptoms and diagnosis of a physician.

EXAMPLES

The following examples are intended to illustrate the present invention, but the scope of the present invention is not limited by the following examples.

Example 1

Acute Toxicity Test in Mice

This test was performed so as to investigate safety of the quinolinone derivatives of the present invention. The test procedure will now be described.
(Test Procedure)

Each of 7-aminoquinolinone derivatives (compounds 32, 53, 55, 56, 58, 87, 147, 173, 181, 204, 236, 276, 303, 309, 330, 359, 396, 401, 459, 514, 519, 546 to 556, and 581) was forcibly administered orally at the doses of 1000 and 2000 mg/kg to male ICR mice (body weight is 20 to 25 g, 5 mice per one group), using feeding tubes for mice.

After the administration, the animals were kept in cages for 7 days. Then, general symptoms were observed and the number of dead animals was counted. 50% lethal dose ($LD_{50}$: mg/kg) was extrapolated from the mortality at 7th day after administration. As a result, the $LD_{50}$ of all aminoquinolinone derivatives was 1000 mg/kg or more, and therefore it was clearly demonstrated that the aminoquinolinone derivatives of the present invention have extremely high safety.

Example 2

This test was performed so as to investigate the pharmacological effect of the 7-aminoquinolinone derivative of the present invention on an airway hyper-responsiveness model induced by exposure of peroxynitrite in guinea pigs. The test procedure will now be described.
(Preparation of Airway Hyper-Responsiveness Model)

Guinea pigs were fasted for 18 hours or more. The animals were administrated the test substance (30 mg/kg) orally one hour before exposure of peroxynitrite and the neck was dissected under ether anesthesia, and then the trachea was exposed. 0.1 mL of 1 mmol/L peroxynitrite was administered intratracheally into pulmonary side by pushing with air and, after the administration, the incision was sutured and disinfected.
(Measurement of Airway Hyper-Responsiveness to Histamine)

The measurement of airway hyper-responsiveness was performed on 5-day, taking the day of model preparation 0-day. Guinea pigs were fasted for 18 hours or more. The measurement of lung resistance; (RLung) was performed according to the method of R. E. Giles et al. (R. E. Giles, M. P. Finkel and J. Mazurowski: Use of an Analog On-Line Computer for the Evaluation of Pulmonary Resistance and Dynamic Compliance in the Anesthetized Dog. Arch. Int. Pharmacodyn. 194, 213-222 (1971)). That is, the animals were anesthetized with Nembutal (Trade name: 40 mg/kg, i.v., sodium pentobarbital) and subjected to cannulation into esophagus, trachea and jugular veins (for administration of histamine). The esophagus and trachea cannulas were connected to an artificial respirator (ventilation volume: 6 mL/kg, ventilation frequency: 60 times/min, SN-480-7) and the Rlung was measured after intravenous administration (dose of 0.1 mL/kg) of physiological saline solution and histamine (32 µg/kg) using a total plethysmograph system via flow sensor, connected to Validyne DF45F (for flow rate) and DP45P (for pressure). RLung before administration was determined by averaging values of any 3 out of 20 breaths, RLung after administration of physiological saline solution was determined by averaging values of any 3 out of 5 breaths, and RLung after administration of histamine was determined by averaging values of the following 3 breaths; 1) showing the maximum lung resistance, 2) taken just before and 3) taken just after the one with the maximum lung resistance, out less than 20 breaths. (The extreme values in RLung that occurred when animal moved during the measurement were excluded from the calculations.)

The percentage of increase in lung resistance was calculated by the following equation.

Increase in lung resistance (%)=([$R$Lung after administration of histamine]−[$R$Lung before administration])/[$R$Lung before administration]×100

TABLE 18

| Compound | Increase (%) |
| --- | --- |
| 32 | 435 |
| 53 | 440 |
| 55 | 425 |
| 56 | 434 |
| 58 | 423 |
| 87 | 432 |
| 147 | 429 |
| 173 | 430 |
| 181 | 425 |
| 204 | 439 |
| 236 | 428 |
| 276 | 430 |
| 303 | 427 |
| 309 | 435 |
| 330 | 417 |
| 359 | 431 |
| 396 | 421 |
| 401 | 420 |
| 459 | 427 |
| 514 | 434 |
| 519 | 440 |
| 546 | 422 |
| 549 | 423 |
| 551 | 416 |
| 553 | 417 |
| 556 | 426 |
| 581 | 430 |
| Control group | 759 |
| Non-stimulation group | 382 |

Increase in lung resistance (%)

From the above results, it was demonstrated that the 7-aminoquinolinone derivatives of the present invention inhibited the resistance to almost the same degree to the non-stimulation group as compared with a control group to which the test substance was not administered. Therefore, it is clear that the 7-aminoquinolinone derivatives of the present invention inhibit an increase in lung resistance induced by peroxynitrite exposure.

Example 3

This test was performed by estimating the antioxidative effect of the test substance using peroxynitrite quantitative method as a test system with dihydrorhodamine 123 so as to confirm the ability of the 7-aminoquinolinone derivatives of the present invention to scavenge peroxynitrite. This is a method described in NITRIC OXIDE: Biology and Chemistry Vol. 1, 145-157, 1997.

The test procedure will now be described.
(Preparation of the Test Substances and Reagents)
1. Preparation of Test Substances The test substance was weighted in an amount of approximately 10 mg, dissolved in a 10% Tween 80 solution and adjusted to $5 \times 10^{-3}$ mol/L. Then, the solution was diluted with 0.1 mol/L phosphate buffer (pH=7.4) to $5 \times 10^{-4}$ mol/L. The diluent was further diluted stepwise with a phosphate buffer containing 1% Tween 80 to obtain substance solution. The preparation was conducted before use. The final concentration of the test substance was adjusted to $3 \times 10^{-6}$, $1 \times 10^{-6}$, $3 \times 10^{-7}$, $1 \times 10^{-7}$, and $3 \times 10^{-8}$ mol/L, respectively.

2. Preparation of Peroxynitrite Solution
1) Measurement of Peroxynitrite Concentration To 20 µL of peroxynitrite solution (manufactured by DOJINDO LABORATORIES), 1980 µL of 0.1 mol/L sodium hydroxide was added and the mixture was diluted 100 times. The absorbance of the maximum absorption wavelength near 300 nm was measured using a UV-visible spectrophotometer and the concentration was calculated according to the following equation.

$$\text{Concentration(mmol/L)} = (\text{absorbance}/1670) \times 100 \times 1000$$

Based on the concentration calculated in the above section, dilution with a 0.1 mol/L sodium hydroxide solution was conducted and adjusted to 10 mmol/L. 990 µL of a 0.1 mol/L sodium hydroxide solution was taken into a 1.5 mL-Eppen tube. To the Eppen tube, 10 µL of a solution adjusted to 10 mmol/L was added to prepare a 100 µmol/L solution.

3. Preparation of Dihydrorhodamine 123 Solution
1) 25 mmol/L Dihydrorhodamine 123 Stock Solution Dihydrorhodamine 123 was dissolved into 1.155 mL of dimethylsulfoxide, and adjusted to the concentration of 25 mmol/L. This solution was dispensed into 20 µL aliquots and then the aliquots were stored in a biomedical freezer (about $-20°$ C.) and used as a stock solution.

2) Preparation of 500 nmol/L dihydrorhodamine 123 solution

To 490 µL of 0.02% Tween 80 containing 0.1 mol/L phosphate buffer, 10 µL of 25 mmol/L of a thawed dihydrorhodamine 123 stock solution was added to make 500 µmol/L. The prepared solution was diluted with 0.1 mol/L phosphate buffer (pH=7.4) 1000 times to prepare 500 nmol/L of a dihydrorhodamine 123 solution.

(Measurement of Peroxynitrite Scavenging Activity)
1. Reaction Operation (1) To a 3.5 mL brown vial containing a stirring bar, 1470 µL of a 500 nmol/L dihydrorhodamine 123 solution and then 15 µL of the test substance solution was added. For the blank and control groups, 15 µL of 0.1 mol/L phosphate buffer containing 1% Tween 80, as a solvent for the test substance solution, was added. After the addition, the mixture was stirred with a stirrer for 30 minutes.

15 µL of a 100 µmol/L peroxynitrite solution was added while stirring. For the blank group, 15 µL of a 0.1 mol/L sodium hydroxide solution was added. After stirring for 15 minutes, fluorescence intensity was measured.

2. Measurement of Fluorescence Intensity

Fluorescence intensity of the reaction solution was measured using a spectrophotofluorometer under the following measuring conditions: excitation wavelength, 500 nm; emission wavelength, 536 nm; measuring times, one; response, 1 sec; photomultiplier tube voltage, Low; band width at excitation side, 10 nm; bandwidth at emission side, 10 nm.

3. Calculation of Oxidation Rate of Dihydrorhodamine 123

The oxidation rate of dihydrorhodamine 123 when adding the test substance was calculated, taking the oxidation rate of dihydrorhodamine 123 for control as 100, according to the following equation:

$$\text{Oxidation rate (\%) of dihydrorhodamine 123} = (\text{measured value for each group} - \text{measured value for blank})/(\text{measured for control} - \text{measured value for blank}) \times 100$$

Calculation of Oxidation Inhibition Concentration ($IC_{50}$)

50% oxidation concentration, that is 50% oxidation inhibition concentration ($IC_{50}$) was calculated by giving a straight line from two points surrounding 50% oxidation rate.

The results are shown in the following table.

TABLE 19

50% Inhibitory concentration on oxidation (IC$_{50}$)

| Compound | Concentration (μmol/L) |
|---|---|
| 32 | 0.96 |
| 53 | 0.88 |
| 55 | 0.96 |
| 56 | 1.05 |
| 58 | 0.81 |
| 87 | 0.84 |
| 147 | 0.79 |
| 173 | 0.89 |
| 181 | 0.94 |
| 204 | 0.89 |
| 236 | 0.88 |
| 276 | 0.82 |
| 303 | 0.84 |
| 309 | 0.80 |
| 330 | 0.79 |
| 359 | 0.85 |
| 396 | 0.94 |
| 401 | 1.01 |
| 459 | 0.94 |
| 514 | 0.91 |
| 519 | 0.83 |
| 546 | 0.79 |
| 549 | 0.80 |
| 551 | 0.71 |
| 553 | 0.98 |
| 556 | 0.89 |
| 581 | 0.76 |

From the above results, it was confirmed that all 7-aminoquinolinone derivatives of the present invention exhibited 50% inhibitory concentration of approximately 1 μmol/L or less, and inhibited the oxidative reaction by peroxynitrite.

Example 4

This test was performed so as to evaluate the pharmacological effect of the 7-aminoquinolinone derivatives of the present invention in an airway hyper-responsiveness model induced by inhalation of ozone in guinea pigs. The test procedure will now be described.
(Preparation of Airway Hyper-Responsiveness Model)

Guinea pigs were fasted for 18 hours or more. The animals were administered the test substance (30 mg/kg) and theophylline (100 mg/kg) one hour before ozone inhalation. For the non-stimulation group and the vehicle control group, vehicle (5 mL/kg) was administered similarly.

The animals were put into an acryl-made chamber (29×19×25 cm), subjected to induction of ozone generated by an ozonizer (EUV3-XU; EBARA JITSUGYO CO, LTD.) and exposed for 2 hours. The ozone concentration in the chamber was approximately 3 ppm. It was confirmed every 30 minutes that this concentration was maintained during exposure by an ozone monitor (EG-5000; EBARA JITSUGYO CO, LTD.) (measured value: 2.53 to 3.40 ppm). For the non-stimulation group, the animals were exposed to a mixed gas (oxygen: 95%, carbonic acid gas: 5%) similarly. The ozone concentration at that time was also confirmed similarly (acceptable concentration: 0.01 ppm or less, measured value: 0.00 to 0.01 ppm).
(Measurement of Airway Hyper-Responsiveness for Methacholine)

The measurement of airway hyper-responsiveness was performed 5 hours after the end of ozone exposure. The measurement of lung resistance (RLung) was performed according to the method of R. E. Giles et al. in the same manner as in Example 2. That is, the animals were anesthetized with Nembutal (Trade name: 50 mg/kg, i.p., sodium pentobarbital) and subjected to cannulation into esophagus and trachea. The esophagus and trachea cannulas were connected to a respirator (ventilation volume: 6 mL/kg, ventilation frequency: 60 times/min, SN-480-7) and the RLung after inhalation of methacholine (100 μg/mL, for 1.5 minutes) was measured by the respiratory function analyzer (PULMOS-II; M.I.P.S) through a flow sensor (connected to Validyle DF45F (for flow rate) and DP45P (for pressure)). The inhalation of methacholine was performed with an ultrasonic nebuliser (NE-U17; Omron Matsuzaka) connected to the respirator under artificial respiration.

Used RLung represents 10 breaths having a stable value in a range from 1 to 30 breaths after initiation of each measurement for both before inhalation and during methacholine inhalation. The average of the RLung was calculated. The extreme values in RLung that occurred when animal moved during the measurement were excluded from the calculations.

The percentage of increase of RLung was calculated by the following equation.

Increase in lung resistance (%)=([$R$Lung after inhalation of methacholine]−[$R$Lung before administration])/[$R$Lung before administration]×100

TABLE 20

Increase in lung resistance (%)

| Compound | Increase (%) |
|---|---|
| 32 | 32 |
| 53 | 29 |
| 55 | 26 |
| 56 | 30 |
| 58 | 27 |
| 87 | 29 |
| 147 | 29 |
| 173 | 30 |
| 181 | 25 |
| 204 | 37 |
| 236 | 28 |
| 276 | 30 |
| 303 | 27 |
| 309 | 34 |
| 330 | 22 |
| 359 | 31 |
| 396 | 22 |
| 401 | 25 |
| 459 | 26 |
| 514 | 31 |
| 519 | 26 |
| 546 | 27 |
| 549 | 28 |
| 551 | 22 |
| 553 | 28 |
| 556 | 25 |
| 581 | 30 |
| Theophylline | 26 |
| Control group | 60 |
| Non-stimulation group | 0 |

From the above results, it was confirmed that the 7-aminoquinolinone derivative of the present invention (dose: 30 mg/kg) showed, in spite of low dose, the effect which is almost equal to or greater than that of an existing drug, theophylline (dose: 100 mg/kg). Therefore, it is clear that the 7-aminoquinolinone derivatives of the present invention inhibit an increase in lung resistance induced by ozone inhalation.

Example 5

5% Powders

| | |
|---|---|
| Compound of the present invention | 50 mg |
| Lactose | 950 mg |
| | 1000 mg |

Preparation example of powders of compounds 32 and 53 will be shown. The compound of the present invention was pulverized in a mortar and thoroughly mixed with lactose. The mixture was poulverized with a pestle to obtain 5% powders of compounds 32 and 53.

Example 6

10% Powders

| | |
|---|---|
| Compound of the present invention | 100 mg |
| Lactose | 900 mg |
| | 1000 mg |

Preparation examples of powders and compounds 236 and 276 will be shown. In the same manner as in Example 5, 10% powders of compounds 236 and 276 were prepared.

Example 7

10% Granules

| | |
|---|---|
| Compound of the present invention | 300 mg |
| Lactose | 2000 mg |
| Starch | 670 mg |
| Gelatin | 30 mg |
| | 3000 mg |

Preparation example of granules of compounds 303, 309, 330 and 359 will be shown. The compound of the present invention was mixed with the equivalent amount of starch and pulverized in a mortar. The mixture was further mixed with lactose and the remaining portion of starch. Separately, 30 mg of gelatin was mixed with 1 ml of purified water, solubilized by heating, cooled and then mixed with 1 ml of ethanol while stirring to prepare a gelatin solution. Thereafter, the mixture prepared above was mixed with the gelatin solution and the resulting mixture was kneaded, granulated, dried and then sized to obtain granules of compounds 303, 309, 330 and 359.

Example 8

5 mg Tablets

| | |
|---|---|
| Compound of the present invention | 5 mg |
| Lactose | 62 mg |
| Starch | 30 mg |
| Talc | 2 mg |
| Magnesium stearate | 1 mg |
| | 100 mg/tablet |

Preparation example of tablets of compounds 514 and 519 will be shown. A 20 times larger portion of the above composition was used to prepare tablets each of which containing 5 mg of the active ingredient. That is, 100 mg of the compound of the present invention in a crystal form was pulverized in a mortar and mixed with lactose and starch. The thus prepared formulation was mixed with 10% starch paste, and the mixture was kneaded and then subjected to granulation. After drying, the resulting granules were mixed with talc and magnesium stearate and then compressed in the usual manner. With the above procedure, tablets of compound 514 and 519 were prepared.

Example 9

10 mg Capsules

| | |
|---|---|
| Compound of the present invention | 300 mg |
| Lactose | 2000 mg |
| Starch | 670 mg |
| Gelatin | 30 mg |
| | 3000 mg |

Preparation example of capsules of compounds 546, 549, 551 and 553 will be shown. Granules were prepared in the same manner as in Example 7 and packed in capsules in 100 mg portions. With the above procedure, capsules of compound 546, 549, 551 and 553 were prepared.

INDUSTRIAL APPLICABILITY

A drug comprising, as an active ingredient, at least one of a 7-aminoquinolinone derivative of the present invention and its physiologically acceptable salt has high safety and exhibits effectiveness against chronic obstructive pulmonary disease and therefore the drug can be utilized medically as a therapeutic agent for chronic obstructive pulmonary disease.

The invention claimed is:

1. A method for treating chronic obstructive pulmonary disease in a warm-blooded animal in need thereof, which comprises orally or parenterally administering to the warm-blooded animal a therapeutic agent for chronic obstructive pulmonary disease comprising, as an active ingredient, a 7-aminoquinolinone derivative represented by the general formula (I):

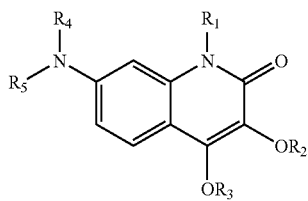

wherein $R_1$ represents a methyl group; $R_2$ represents an octyl group; $R_3$ represents a hydrogen atom; $R_4$ represents a hydrogen atom; and $R_5$ represents a 3,5-dimethoxy-4-hydroxycinnamoyl group, and its physiologically acceptable salt,
wherein a dose as an amount of active ingredient is from 0.01 to 50 mg per day per 1 kg of body weight in the case of oral administration, the dose as the amount of active ingredient is from 0.01 to 10 mg per day per 1 kg of body weight in the case of parenteral administration.

2. The method for treating chronic obstructive pulmonary disease according to claim 1, wherein the chronic obstructive pulmonary disease is chronic bronchitis.

3. The method for treating chronic obstructive pulmonary disease according to claim 1, wherein the chronic obstructive pulmonary disease is pulmonary emphysema.

4. The method for treating chronic obstructive pulmonary disease according to claim 1, wherein said therapeutic agent for chronic obstructive pulmonary disease is orally administered.

5. The method for treating chronic obstructive pulmonary disease according to claim 1, wherein said therapeutic agent for chronic obstructive pulmonary disease is taken internally.

6. The method for treating chronic obstructive pulmonary disease according to claim 1, wherein said therapeutic agent for chronic obstructive pulmonary disease is orally administered to treat pulmonary emphysema.

7. The method for treating chronic obstructive pulmonary disease according to claim 1, wherein said therapeutic agent for chronic obstructive pulmonary disease is orally administrated to improve lung resistance.

8. The method for treating chronic obstructive pulmonary disease according to claim 1, wherein said therapeutic agent for chronic obstructive pulmonary disease is parenterally administrated to inhibit infiltration of inflammatory cells into airway.

9. The method for treating chronic obstructive pulmonary disease according to claim 2, wherein said therapeutic agent for chronic obstructive pulmonary disease is orally administrated to improve lung resistance.

10. The method for treating chronic obstructive pulmonary disease according to claim 2, wherein said therapeutic agent for chronic obstructive pulmonary disease is orally administrated to improve residual volume.

11. The method for treating chronic obstructive pulmonary disease according to claim 2, wherein said therapeutic agent for chronic obstructive pulmonary disease is parenterally administrated to inhibit infiltration of inflammatory cells into airway.

12. The method for treating chronic obstructive pulmonary disease according to claim 3, wherein said therapeutic agent for chronic obstructive pulmonary disease is orally administrated to improve lung resistance.

13. The method for treating chronic obstructive pulmonary disease according to claim 3, wherein said therapeutic agent for chronic obstructive pulmonary disease is orally administrated to improve residual volume.

14. The method for treating chronic obstructive pulmonary disease according to claim 3, wherein said therapeutic agent for chronic obstructive pulmonary disease is parenterally administrated to inhibit infiltration of inflammatory cells into airway.

* * * * *